United States Patent [19]

Moore

[11] Plant 5,110

[45] Sep. 27, 1983

[54] ROSE PLANT

[75] Inventor: Ralph S. Moore, Visalia, Calif.

[73] Assignee: Sequoia Nursery, Visalia, Calif.

[21] Appl. No.: 342,119

[22] Filed: Jan. 25, 1982

[51] Int. Cl.[3] ..... A01H 5/00

[52] U.S. Cl. ..... Plt./7

[58] Field of Search ..... Plt./7

*Primary Examiner*—Robert E. Bagwill

[57] ABSTRACT

This invention relates to a new and distinct variety of miniature rose plant, primarily identified by its flowers of unique form and coloring — the petals being folded (quilled) to a point and the color being a blending of red, yellow and coral.

1 Drawing Figure

1

The present invention relates to a new and distinct variety of hardy, dwarf, bush type rose plant of the miniature class; the variety being primarily characterized — as to novelty — by the unique blending of yellow overlaid with a deep to medium coral red color (or colors).

The variety is further characterized by:

An abundance of bloom, with flowers usually borne singly, but also several to the stem in small cluster.

Some fragrance.

A plant which is vigorous, of rounded to spreading shape with small semi-glossy to matt foliage with pointed leaflets; the buds and flowers being similar in form to Over the Rainbow (miniature — U.S. Plant Pat. No. 3,472) but slightly larger in size.

The plant, which has a normal height of 14–16 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery Located at Visalia, Calif., under conditions of careful control and observation, as a cross between Golden Glow (Brownell — U.S. Plant Pat. No. 263 — expired) as the seed parent and Over the Rainbow (miniature — U.S. Plant Pat. No. 3,472) as the pollen parent.

Subsequent to origination of the variety I successfully asexually reproduced it at Sequoia Nursery, located as aforesaid, by budding as well as by cuttings; the reproductions having run true in all respects.

The color photograph illustrates the variety, including the foliage, buds and flowers (Note: Color photo shows flower at its deepest color — usually comes less red, depending upon light intensity and temperature. In cooler weather colors may be more pink and outer petals show slight magenta tone).

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; spreading; seedling; greenhouse; outdoors; cut flowers; garden decoration; potted plant.

Class: Miniature.

2

*Variety identification.*—MORnita (Commercial synonym: Anita Charles).

Flowers borne: Singly and several together (3 to 5) on slender wirey stems.

Quantity of bloom: Abundant both outside and in greenhouse.

Bud:

*Peduncle.*—Medium to short length; slender but sturdy; erect; medium green, sometimes tinted bronze (outdoors); with no prickles and few or no hairs.

*Before calyx breaks.*—Size — Small.

*Form.*—Long, pointed, with several small foliaceous apendages on surface of bud; with foliaceous parts extending beyond the tip of the bud equal to one-half or more of its length.

*Color.*—Medium green, occasionally tinted with bronze (outdoors).

*As calyx breaks.*—Color — reddish (sometimes greenish yellow).

*Opening.*—Opens well in all weather.

Bloom:

*Size when fully open.*—Small, averaging about 40–45 mm ($1\frac{1}{2}$–$1\frac{3}{4}$").

*Petalage.*—Double — averaging about 30–35 (or more) petals, arranged regularly plus several small petaloids.

*Form.*—Cupped at first becoming more rounded with petals rolled slightly outward and downward. Open flowers usually have stamens.

Petals: Fairly thick; satiny on inside and on outside surface.

*Shape.*—Outside petals, broad lanceolate with nearly round tip or very short acute tip; intermediate — broad lanceolate with nearly round or short acute tip; inside — lanceolate with acute tip. (Note; Petals fold and become pointed (quilled) as in an Hybrid Cactus Dahlia Flower).

Color: Newly opened flower from a plant grown in plastic greenhouse (July 1980), Visalia, Calif.

*Outside petal.*—Outside surface — yellow with color of upper surface bleeding through to give a color effect near Scarlet 19/1 or Geranium Lake 20/2 (or lighter), but with more yellow — a color commonly called deep coral or coral-red (also giving a tanish gold effect). Bright yellow at base — also there may be a hint of lavender or magenta on outer petals as they mature. Inside surface — near Geranium Lake 20 or 20/1 (sometimes darker) laid over yellow to give a general deep red — coral effect — with narrow yellow or gold band along margin of each petal; bright yellow on basal ¼ of petal.

*Intermediate petal.*—Outside surface similar to outside petal except red color is underlaid with more yellow. Inside surface similar to outside petal.

*Inner petal.*—Outside surface — similar to intermediate petal; inside surface — similar to intermediate petal.

In warmer weather all petals generally show more yellow, especially on lower (reverse) side which give flowers a bi-color effect. (Color photo made in September 1980).

General color effect: Buds and newly opened flowers — coral/red blended with yellow, often with a gold/-tan effect.

*Three days open.*—Color similar to fresh open flowers, but less bright.

*Behavior.*—Opens well in all weather. Spent petals or flowers drop off.

*Flower longevity (July–August* 1980).—Plant in pot 6–10 days or longer. Cut flowers at living room temperature 5–7 days or longer.

Reproductive organs:

*Stamens.*—Average number.

*Filaments.*—Varying length — fairly short.

*Anthers.*—Yellow.

*Pollen.*—Quite abundant.

*Pistils.*—Average number.

*Styles.*—Varying length; near white to pale yellow; bunched.

*Ovaries.*—All enclosed in calyx.

*Hips.*—Some.

*Sepals.*—Permanent; spear shaped; recurved.

*Seed.*—Few.

Foliage:

*Leaves.*—Compound of five (sometimes three or seven) leaflets; medium small; leathery; semi-glossy to matt.

*Leaflets.*—Shape; broad; lanceolate; apex acute; base — acute — sometimes rounded. Color: medium green; new growth — normal (medium) green (sometimes tinted reddish). Rachis: medium strength; upper side may have a few short hairs; grooved; underside may have several small thorns (or claws) and few or no short prickles. Stipules: medium length; medium width; medium to short length narrow points which turn out usually at about 45 degrees or more.

Growth:

*Habit.*—Dwarf; bushy; rounded; spreading; much branched.

*Growth.*—Vigorous; internodes short.

*Canes.*—Medium; slender; sturdy.

*Main stems.*—Color: medium green.

*Thorns.*—Several — medium length; brown; nearly straight — inclined downward. Hairs — few or none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded, much branched habit, substantially as illustrated and described, characterized by buds and flowers similar in form to Over the Rainbow (miniature — U.S. Plant Pat. No. 3,472) but slightly larger in size, the color being a blend of red, coral and yellow, the upper side of petals being deeper color than lower side, giving the flower a bi-color effect and (a) the open petals becoming quilled (pointed as in a Hybrid Cactus type Dahlia); (b) each petal having a narrow gold (or yellow) margin, and further characterized by a vigorous, compact plant, usually broader than tall, the said plant being easy to propagate from softwood cuttings, with an abundance of small semi-glossy to matt foliage, the flowers being born singly or several to the stem in loose spray or cluster.

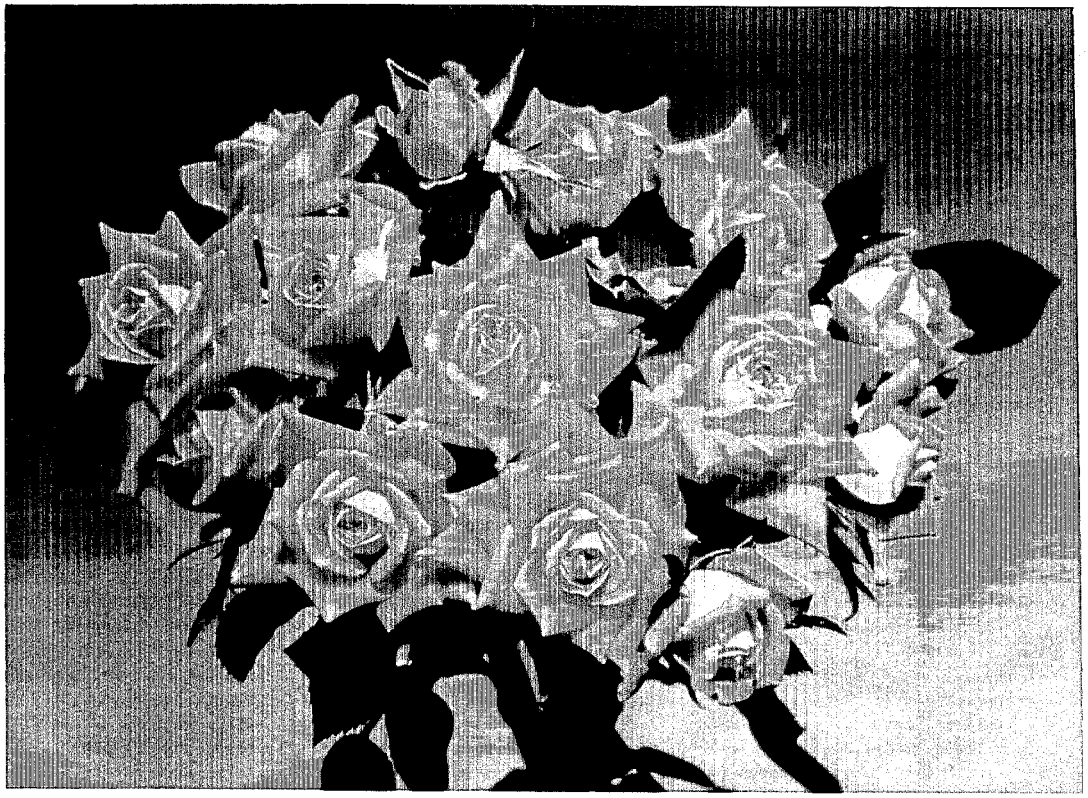

* * * * *